United States Patent [19]
Bischoff et al.

[11] Patent Number: 5,347,708
[45] Date of Patent: Sep. 20, 1994

[54] METHOD FOR FABRICATION OF IMPLANTABLE ELECTRODE

[75] Inventors: Thomas C. Bischoff, Minneapolis; Pedro A. Meregotte, Coon Rapids; David P. Morell, Cambridge, all of Minn.

[73] Assignee: Medtronic, Inc., Minneapolis, Minn.

[21] Appl. No.: 125,093

[22] Filed: Sep. 21, 1993

[51] Int. Cl.⁵ ............................................. H01R 43/00
[52] U.S. Cl. ........................................ 29/825; 29/605; 427/120
[58] Field of Search ................ 29/825, 605; 427/120; 428/419 P, 789; 128/786, 784

[56] References Cited

U.S. PATENT DOCUMENTS

| | | |
|---|---|---|
| 4,106,512 | 8/1978 | Bisping . |
| 4,161,952 | 7/1979 | Kinney . |
| 4,258,725 | 3/1981 | O'Neill . |
| 4,502,492 | 3/1985 | Bornzin . |
| 4,506,680 | 3/1985 | Stokes . |
| 4,817,634 | 4/1989 | Holleman . |
| 4,922,607 | 5/1990 | Doan . |
| 4,934,049 | 6/1990 | Kiekhafer . |
| 5,042,143 | 8/1991 | Holleman . |

Primary Examiner—Carl J. Arbes
Attorney, Agent, or Firm—Reed A. Duthler; Harold R. Patton

[57] ABSTRACT

An implantable electrode of the type in which an elongated wire coil forms the electrode surface. The electrode coil is mounted around an insulative lead body and is stabilized on the lead body by means of a plastic filler between the individual turns of the electrode coil, extending radially outwardly to approximately one-third of the diameter of the electrode coil wire. The filler is produced by stretching a portion of the lead body which normally displays an outer diameter greater than the inner diameter of the electrode coil sliding the electrode coil over the lead body, inserting an expandable mandrel into the lead body and expanding the mandrel to urge the lead body into contact with the electrode coil. This assembly is then heated to encourage flow of the lead body into the spaces between the electrode coil to stabilize the coil on electrode body and to present fibrotic ingrowth around the electrode coil wire.

8 Claims, 2 Drawing Sheets

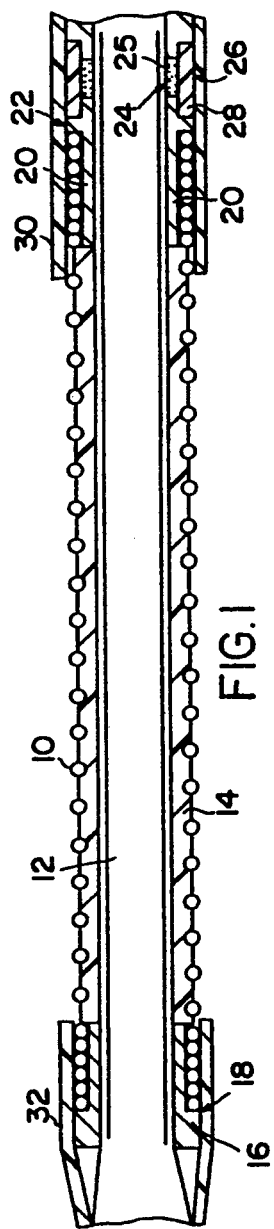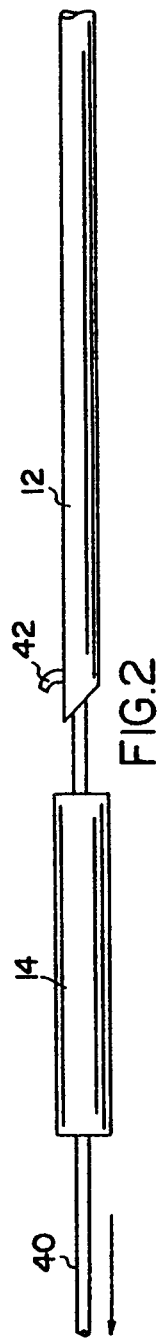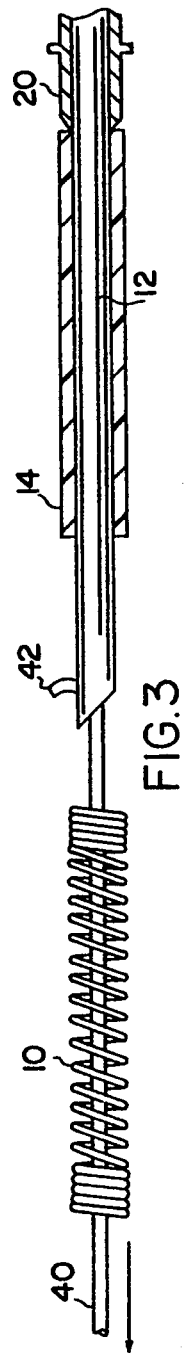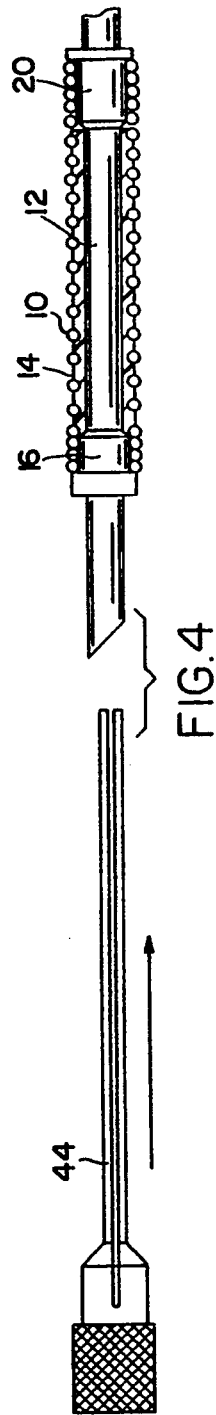

METHOD FOR FABRICATION OF IMPLANTABLE ELECTRODE

BACKGROUND OF THE INVENTION

This invention relates to medical electrical stimulation electrodes in general and to defibrillation electrodes in particular.

In the past years, there has been substantial activity toward development of a practical implantable defibrillator. Most proposals involve the use of large surface area implantable electrodes either to be mounted within the heart, on the exterior of the heart or subcutaneously. One common approach of providing a large surface area electrode is to employ an elongated exposed coil of biocompatible metal. In the context of an endocardial lead, this is disclosed in U.S. Pat. No. 4,161,952 issued to Kinney. In the context of an epicardial lead, this is disclosed in the context of U.S. Pat. No. 4,817,634 issued to Holleman et al.

In an epicardial lead, an elongated coil serving as the electrode can be mounted around the exterior of an insulative lead body. It is believed desirable in this context to stabilize the electrode coil with respect to the lead body, both to provide mechanical integrity and to prevent fibrous ingrowth around the individual coils of the electrode coil. In the above cited Kinney et al. patent, this is accomplished by sliding the coil over the lead body and backfilling the spaces between the electrode coil with a plastic material. The exterior surface of the electrode is then machined to provide a smooth surface. Alternatively, the backfilling may be removed by means of a plasma etch as disclosed in commonly assigned U.S. Pat. No. 4,934,049, issued to Keikhafer et al., for a "Method for Fabrication of a Medical Electrode". In this application, the backfilling is illustrated as extending radially outward between the turns of the coil about one-third to one-half the diameter of the coil wire. This patent is incorporated herein by reference in its entirety.

In prior U.S. Pat. No. 5,042,143 issued to Holleman et al., an alternative method of producing a lead structure similar to that produced in the Keikhafer patent, but without the necessity of using a backfilling, to produce a defibrillation lead employing polyurethane to stabilize the electrode coil and to fill between the turns of the coil. In the Holleman et al. patent, a plastic tube is stretched so that it displays an inner and outer diameter less than the inner and outer diameter of the tube in a relaxed state. An electrode coil having a inner diameter less than the outer diameter of the tube in its relaxed state is then slide over the stretched tube, after which the tube, after which the tube is released, allowing it to return to its previous length. However, the tube remains in a compressed state, throughout the length of the electrode coil, Thereafter, a mandrel having an outer diameter greater than the inner diameter of the tubing in its compressed state is passed into the tubing, to compress the tubing between the mandrel and the conductor coil. The assembly is thereafter heated, allowing the tubing to flow into spaces between the electrode coil.

SUMMARY OF THE INVENTION

The present invention is directed toward an improvement to the method of electrode fabrication disclosed in the above-cited Holleman et al. patent. In practice, it has been found that insertion of a mandrel of the type disclosed in the Holleman patent, while workable, presents some practical difficulties. In particular, it has been determined that the approach disclosed in Holleman et al., in which the mandrel is forced into the tubing, is results in variability of the pressure applied between the mandrel and the electrode coil, producing an uneven structure in which the tubing does not flow outward to a consistent dimension, between the electrode coils.

The present invention addresses this difficulty by means of an expandable mandrel, which in its unexpanded form has an outer diameter less than the inner diameter of the tubing in its compressed form, and which is expanded to display an outer diameter approximately equal to the inner diameter of the tubing in its relaxed state. Because the mandrel is inserted without excessive frictional engagement with inner surface of the lumen of the tube, longitudinal compressive forces are avoided, allowing for provision of consistent compressive forces between the mandrel and the electrode coil, when the mandrel is expanded.

Expansion of the mandrel is accomplished by advancing a rod through the internal lumen of the mandrel tube, the rod having an outer diameter greater than the inner diameter of the mandrel tube in its relaxed state. In the specific embodiment disclosed, the rod is provided with threads, allowing it to be screwed into and along the mandrel tube.

BRIEF DESCRIPTION OF THE DRAWINGS

FIG. 1 illustrates a side cutaway view through a defibrillation electrode manufactured according to the present invention, FIG. 2 illustrates an initial step of the manufacture of the electrode illustrated in FIG. 1.

FIGS. 2, 3 and 4 illustrate various points within the process of assembly of the electrode illustrated in FIG. 1.

DETAILED DESCRIPTION OF THE INVENTION

Figure 5:
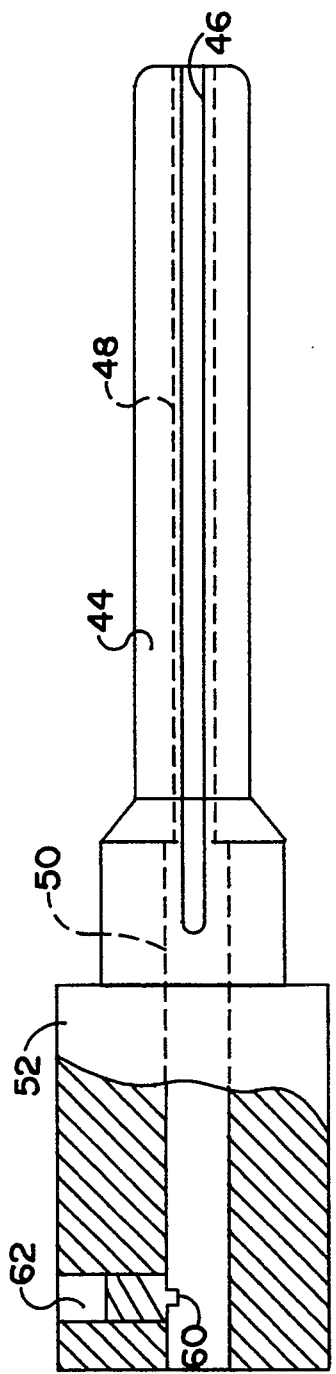
FIGS. 5 and 6 illustrate the structure of the expanding mandrel.

FIG. 1 is a side cutaway view through an endocardial defibrillation electrode according to the present invention. The electrode coil 10 is a space wound, single filar coil of platinum mounted around insulative tubing 12. Between the coil 10 and the tubing 12 and between the individual turns of the coil 10 is a filler plastic tube 14 which is preferably insulative, but may be conductive plastic in some cases. The filler plastic tube 14 extends radially outward from the sheath 12 between the individual turns of coil 10 and typically extends outward between the individual turns of coil 10 to a distance of approximately one-third the diameter of the wire from which coil 10 is fabricated.

Tube 14 and tubing 12 are preferably fabricated of an implantable elastic plastic, preferably a polyurethane. Tube 14 and tubing 12 together form the lead body in the vicinity of electrode coil 10. At its distal end coil 10 is coupled to a welding sleeve 16 by means of a laser weld at shoulder 18. Similarly at its proximal end coil 10 is coupled to transition sleeve 20 by means of a laser weld at shoulder 22. Welding sleeve 16 and transitional sleeve 20 are both preferably fabricated of an inert, conductive metal such as platinum to which coil 10 may be readily welded. Transitional sleeve 20 is provided with two perpendicular bores 24 and a circumferential groove 26. A band 28 of insulative material preferably polyurethane, fills circumferential groove 26, and bores 24 are backfilled with an appropriate adhesive to attach band 28 to tubing 12 assisting in stabilizing the electrode assembly. Transitional sleeve 20 extends proximally into contact with an elongated coiled conductor (not illustrated) extending to the proximal end of the lead. This conductor serves to couple defibrillation electrode 10 to an implantable defibrillator and may be manufactured using any conventional technique known to the art and coupled to transitional sleeve 20 using any conventional technique known to the art such as crimping, welding, etc. Surrounding the proximal portion of electrode coil 10 is an outer insulative sheath 30 which extends proximally to the proximal end of the lead, covering the coil coupled to transitional sleeve 20.

At the distal end of the lead, an outer insulative sheath 32 covers the distal end of electrode coil 10 and may extend distally to one or more pacing electrodes coupled to conductors within tubing 12. In the preferred embodiment of the present invention, outer insulative sheaths 30 and 32 are fabricated of an polyurethane of one of the types typically used in conjunction with cardiac pacing leads and are preferably mechanically coupled to the proximal and distal ends of electrode coil 10 by means of an adhesive to further stabilize their locations.

FIG. 2 illustrates an early step in the manufacture of a defibrillation electrode according to the present invention. In this early step, tube 12 is attached to a holding fixture at its proximal end (not illustrated) and filler tube 14 is slid over a stylet 40. Stylet 40 is provided with a hooked end 42 passed through the distal end of tubing 12.

Preferably tubing 12 displays an outer diameter somewhat greater than the inner diameter of filler tube 14. For example, tubing 12 may be 0.068"×0.082" Pellethane ® 2363-80A polyurethane, and filler tube 14 may be a 0.079"×0.095" tube fabricated of the same material.

Filler tube 14 is placed over stylet 40. The hooked end of styler 40 is passed through the wall of tubing 12 and used to extend the wall of tubing 12 until the diameter of tubing 12 has decreased sufficiently to slide filler tube 10 over tubing 12. Preferably, approximately 1½" of tubing 12 extends distal to filler tube 14. Freon may be used to lubricate tubing 12 to facilitate this step, if necessary.

The assembly of tubing 12 and filler tube 14 is then allowed to air dry for approximately ½ hour and a urethane adhesive is then backfilled between filler tube 14 and tubing 12 at the proximal and distal ends of filler tubing 14.

This assembly is allowed to air dry and is placed in an oven under nitrogen purge. The oven temperature is gradually increased to 150° C. After about five to ten minutes at 150° C., the oven is shut off, and the temperature allowed to fall. This heating step relieves any stresses built up in the tubing. The tubing is removed from the oven and allowed to cool to room temperature.

FIG. 3 illustrates a later step in the assembly process. Prior to this step, the transition sleeve 20 has been located adjacent the proximal end of filler tubing 14. Electrode coil 10 preferably has an inner diameter less than the outer diameter of the assembly comprising tubing 12 and filler tubing 14. Coil 10 may be a space would coil of platinum wire and may have an inner diameter of 0.092". Coil 10 is placed over styler 40, and the hooked distal end 42 of stylet 40 is again passed through the distal end of tubing 12. Stylet 40 is used to stretch tubing 12 and filler tube 14, allowing coil 10 to be slid proximally over filler tube 14 until its proximal end abuts the circumferential shoulder 22 of transition sleeve 20. Tubing 12 and tube 14 are then allowed to relax and re-expand into contact with the interior of electrode coil 10.

FIG. 4 illustrates a subsequent step in the process of manufacture of the electrode and shows welding sleeve 16 slipped over tubing 12 inside the distal end of electrode coil 10. At this point, the inner diameter of tubing 12 is less than its normal inner diameter as tubing 12 and filler tube 14 are under radial compression by electrode coil 10. Teflon coated mandrel 44 has an outer diameter less than the inner diameter of tubing 10 in its compressed state. Mandrel 44 is lubricated with alcohol and slid into the interior of tubing 10. The outer diameter of mandrel 44 is then increased to a diameter approximately equal to the inner diameter of tubing 10 in its relaxed state. This serves to compress tubing 10 and filler tubing 14 against the interior coil 10. This assembly is allowed to air dry and is then placed into an oven gradually heated to 150° C. under nitrogen purge in order to cause flow of filler tube 14 between the individual turns of electrode coil 10 to produce the structure illustrated in FIG. 1 above. After about five to ten minutes at 150° C., the oven is turned off and the temperature is allowed to gradually fall. The assembly is then removed from the oven, allowed to cool at least 30 minutes and the mandrel is removed.

Preferably, the relative sizes of tubing 12, filler tubing 14 and electrode coil 10 should be such that after this baking step, material from filer tube 14 extend radially within the spaces between the individual turns electrode coil 10 a distance of approximately one-third to one-half of the diameter of the wire from which electrode coil 10 is fabricated.

Figure 6:
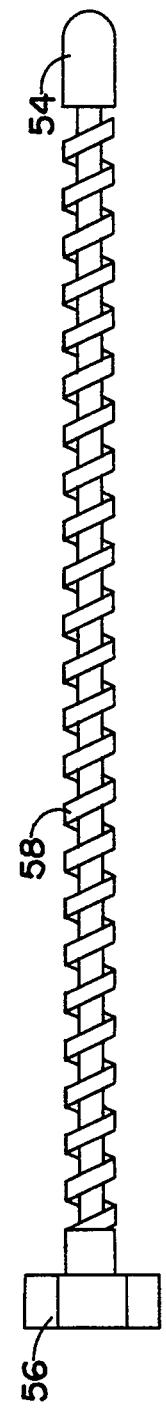

FIG. 5 illustrates the expandable tube of the mandrel according to the present invention, and associated structure. Expandable tube 44 is provided with a longitudinal slot 46, shown as running longitudinally along tube 44, through one wall. Alternatively, a second slot may also be provided, diametrically opposite to slot 46. At the proximal end of mandrel tube 44, a neural knob 52 is located, having a central bore 50, which receives the threaded rod illustrated in FIG. 6. The internal diameter of lumen 50 within knob 52 is slightly greater than the outer diameter of the threaded rod illustrated in FIG. 6. The rod illustrated in FIG. 6 is provided with square cut threads 58, which engage with a pin 60, mounted to a threaded plug 62. Rotation of the bolt head 56 located at the proximal end of the rod of FIG. 6 causes it to advance within the lumen 50 of the handle 52 as well as within the lumen 48 of mandrel tubing 44. The outer diameter of the threaded rod in FIG. 6 is slightly greater than the inner diameter of lumen 48 within mandrel 44, whereby tubing 44 is expanded as the rod passes along its length. The distal end 54 of the threaded rod is provided with a rounded tip, facilitating its passage through the internal lumen of mandrel tubing 44. Threaded plug 62 may be removed, allowing replacement of the pin 60 when worn, or to allow removal of the threaded rod by simply pulling the rod in approximate direction. Advancement of the threaded rod of FIG. 6 into the expandable mandrel tubing 44 occurs after insertion of mandrel tubing 44 into the interior of tubing 12, passing through the coil electrode 10. The threaded rod of FIG. 6 may be removed from the expandable tubing 44 of the mandrel before or after removal of the mandrel from tubing 12. Removal of the threaded rod prior to removal of the mandrel facilitates removal of the mandrel tube, without the necessity of injection of air or alcohol, are required in conjunction with the non-expandable mandrel employed in the above-cited Holleman et al. patent.

The remainder of the assembly of the lead typically follows the completion of this step and would include laser welding of the electrode 10 to sleeve 20, inserting sleeve 16 into the electrode 10, coupling of a conductor coil to the proximal end of sleeve 20 and location of outer insulative sheaths 30 and 32 overlapping the proximal and distal ends, respectively, of electrode coil 10 as illustrated in FIG. 1. Assembly of the remainder of the lead may also optionally include the provision of one or more pacing electrodes at the distal end of the lead and will include the provision of an electrical connector assembly at the proximal end of the lead. Addition of these assemblies to the lead may be accomplished using any of a number of available prior art structures and manufacturing techniques such as those disclosed in U.S. Pat. Nos. 4,506,680, 4,502,492, 4,258,725, 4,106,512, or U.S. Pat. No. 4,922,607, issued to Doan et al. for a "Connector for Multiconductor Leads", all of which are incorporated herein by reference. However, it is believed that one of skill in the art would readily appreciate that the present invention can be applied to any elongated medical electrical lead employing any desired combination of additional electrodes, sensors and connectors.

As such, the embodiments illustrated above should be considered exemplary rather than limiting with regard to the scope of the following claims.

In conjunction with the above specification, we claim:

1. A method of fabricating a medical electrical electrode comprising the steps of:
   sliding an elongated conductive coil over a length of plastic tubing;
   inserting an expandable mandrel within said plastic tubing and expanding said mandrel to expand said tubing against said coil and to compress said tubing between said mandrel and said coil; and
   heating the assembly of said mandrel, said tubing and said coil to cause flow of said plastic tubing between individual turns of said coil.

2. A method of fabrication according to claim 1, wherein said elongated conductive coil has an inner diameter and wherein said plastic tubing comprises an elastic plastic and has an outer diameter greater than the inner diameter of said conductor coil, and wherein said method further comprises the step of stretching said plastic tubing to reduce the diameter of said tubing prior to sliding said conductive coil over said plastic tubing.

3. A method according to claim 1 wherein said plastic tubing comprises a first elongated plastic tube, surrounded by a second plastic tube having substantially shorter length than said first plastic tube, and adhered to said first plastic tube, and wherein said step of sliding said coil over said plastic tubing comprises sliding said coil over said second plastic tube.

4. A method according to claim 1 wherein said expandable mandrel has an outer diameter in an unexpanded state and wherein said plastic tubing has an inner diameter greater than the outer diameter of said expandable, mandrel in said unexpanded state and wherein said step of expanding said mandrel comprises expanding said mandrel to an outer diameter greater than the inner diameter of said plastic tubing.

5. A method of fabrication of a medical electrode comprising the steps of:
   sliding a first plastic tube over a second, substantially longer plastic tube;
   sliding a conductive coil over said first plastic tube;
   inserting an expandable mandrel within said second plastic tube and expanding said mandrel to expand said first and second plastic tubes and to compress said first and second plastic tubes between said mandrel and said coil; and
   heating the assembly of said mandrel, said first and second tubes and said coil to allow the material of said first tube to flow between individual turns of said coil.

6. A method according to claim 5 wherein said first and second plastic tubes comprise elastic plastic tubes, wherein said first plastic tube has an inner diameter and wherein said second plastic tube has an outer diameter greater than the inner diameter of said first plastic tube, and wherein said method comprises the additional step of stretching said second plastic tube to reduce its outer diameter prior to said step of sliding said second plastic tube over said first plastic tube.

7. A method according to claim 5 or claim 6 wherein said conductive coil has an inner diameter and wherein said first and second plastic tubes are elastic plastic tubes, said first plastic tube having an outer diameter, in its relaxed state, greater than the inner diameter of said conductive coil, and wherein said method comprises the further step of stretching said first and second plastic tubes to reduce the outer diameter of said first plastic tube prior to said step of sliding said conductive coil over said first plastic tube.

8. A method according to claim 5 wherein said expandable mandrel has an outer diameter in an unexpanded state and wherein said second plastic tube has an inner diameter greater than the outer diameter of said expandable mandrel in said unexpanded state and wherein said step of expanding said mandrel comprises expanding said mandrel to an outer diameter greater than the inner diameter of said second tube.

* * * * *